United States Patent [19]

Kruse et al.

[11] Patent Number: 4,482,755

[45] Date of Patent: Nov. 13, 1984

[54] HIGH YIELD PROCESS FOR PREPARING 4,4'-BIPHENOL AND PARA-ALKYLBENZENES

[75] Inventors: Walter M. Kruse, Wilmington, Del.; John F. Stephen, West Chester, Pa.

[73] Assignee: ICI Americas Inc., Wilmington, Del.

[21] Appl. No.: 514,253

[22] Filed: Jul. 15, 1983

[51] Int. Cl.³ .............................................. C07C 39/15
[52] U.S. Cl. ..................................... 568/730; 585/319
[58] Field of Search ................. 568/730; 585/310, 319

[56] References Cited

U.S. PATENT DOCUMENTS

| | | | |
|---|---|---|---|
| 2,792,427 | 5/1957 | Houtson et al. | 260/613 |
| 3,306,875 | 2/1962 | Hay | 568/730 |
| 3,562,338 | 2/1971 | Zaweski | 260/620 |
| 3,631,208 | 12/1971 | Hay | 260/619 R |
| 3,748,303 | 7/1973 | Becker | 568/730 |
| 4,100,205 | 7/1978 | Rutledge | 568/730 |
| 4,101,561 | 7/1978 | Rutledge | 260/396 |
| 4,108,908 | 8/1978 | Rutledge | 568/730 |
| 4,132,722 | 1/1979 | Rutledge | 260/206 |
| 4,139,544 | 2/1979 | Rutledge | 260/396 |
| 4,195,189 | 2/1979 | Earley | 568/730 |
| 4,205,187 | 5/1980 | Gardenas et al. | 563/730 |
| 4,354,047 | 10/1982 | Strom | 568/730 |
| 4,354,048 | 10/1982 | Strom | 568/730 |
| 4,414,422 | 11/1983 | Ash et al. | 568/724 |

OTHER PUBLICATIONS

M. Tashiro, "Selective Synthesis of Aromatic Cmpds. Using Positional Protective Groups," *Synthesis* (1979) pp. 921-924.

*Primary Examiner*—Werren B. Lone
*Attorney, Agent, or Firm*—Richard A. Rowe

[57] ABSTRACT

4,4'-biphenol and tert-alkyl substituted alkyl benzene derivatives are produced by hydrogenating a tetraalkyl diphenoquinone in an alkyl benzene solvent solution under relatively mild conditions in the presence of a heterogeneous catalyst, removing said catalyst from the resultant tetraalkyl biphenol and thereafter heating said alkyl benzene solvent solution in the presence of a strong acid catalyst to form relatively pure biphenol in high yields and a para substituted alkyl benzene derivative.

11 Claims, No Drawings

HIGH YIELD PROCESS FOR PREPARING 4,4'-BIPHENOL AND PARA-ALKYLBENZENES

The invention relates to a new improved process for hydrogenating 3,3',5,5'-tetra-alkyl-4,4'-diphenoquinone to the corresponding diphenol and the subsequent dealkylation thereof in the presence of an alkylbenzene to provide a high yield of completely dealkylated biphenol and a para substituted tert-alkyl-alkylbenzene derivative.

Biphenols, and particularly substituted biphenols have wide utility as bactericides, chemical intermediates, as monomers in making copolymers and as antioxidants. The 2,6-disubstituted biphenols are used to stabilize such materials as animal and vegetable fats or oils, gasoline, lubricants, rubber compositions and as monomers for the preparation of high performance resins. Moreover unsubstituted biphenols such as 4,4'-biphenol is a very useful monomer in the preparation of high performance resins such as polysulfones, polyketones, polycarbonates, polyesters and polyurethanes wherein the biphenol is used as the dihydroxyl compound which is reacted with phosgene, dibasic acids, polyepoxides and polyisocyanates etc. When used in this way aromatic resins are produced which exhibit good physical mechanical products combined with superior oxidation and solvent resistance.

The tert-alkylated alkylbenzenes are also useful products and as for example tert-butylethylbenzene which is an intermediate in the synthesis of tert-butyl styrene, a valuable monomer in the manufacture of modified styrene resins as described in U.S. Pat. No. 4,334,115. Additional intermediates such as tert-butyltoluene can be made economically for use in fragrances and insecticide.

Previously biphenols have been rather difficult and costly to produce because of the involved procedures required, the tendency to produce undesirable by-products, the difficulty in obtaining a pure product and color characteristics needed for resin use, low yield and the necessity for employing expensive equipment. As a result of the present invention both 4,4'-bis(2,6-di-tert-butylphenol) or 4,4'-biphenol along with a valuable coproduct such as a tertiary-butylated alkyl aromatic hydrocarbon can be produced in high yields in relatively inexpensive equipment at low temperatures and pressures.

Previously tetrasubstituted biphenols have been generally prepared by the oxidative dimerization of disubstituted phenol reactants in the presence of a metallic or strongly alkaline catalyst to form the corresponding tetrasubstituted diphenoquinone. The quinones are recovered and then reduced with hydrogen to the corresponding substituted biphenol. More recent descriptions of these reactions can be found in U.S. Pat. Nos. 4,354,047; 4,354,048; 4,205,187; 4,085,124 and 4,096,190.

It is an object of the present invention to provide for an improved process for carrying out the hydrogenation of a tetra-substituted diphenoquinone to form the corresponding tetra-substituted biphenol in high yields. It is another object to provide a transalkylation process of tetra-alkylbiphenol in alkylbenezene solution to provide high yields of biphenol and para tert-alkylated alkylbenezene. Another object is to provide an integrated process for forming biphenol and an R-alkylated alkyl benzene derivative from an alkylbenzene solution of a tetra-substituted diphenoquinone characterized by the steps:

(a) forming a tetraalkyl biphenol by the hydrogenation of a diphenoquinone having the general formula:

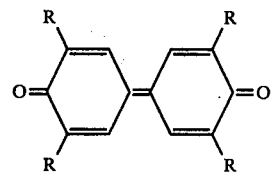

wherein R is a tertiary alkyl group having 4–8 carbon atoms employing hydrogen gas and a heterogeneous catalyst in a solvent solution of an alkyl benzene, (b) removing said catalyst from the tetraalkyl biphenol containing solution, (c) heating said solution in the presence of a strong acid catalyst in an inert atmosphere to form biphenol and an R substituted tert-alkyl-alkylbenzene derivative, and (d) recovering biphenol and said R-substituted alkyl benzene from said solution.

The hydrogenation step is carried out in an alkylbenzene solvent solution of a diphenoquinone having the general formula:

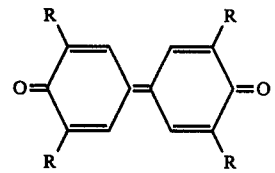

wherein R is a tertiary alkyl group having 4 to 8 carbon atoms such as tert-butyl, tert pentyl, and tert-octyl. The diphenoquinone materials are readily obtainable by the oxidative coupling of the corresponding 2,6-dialkylphenol derivatives in the presence of an appropriate oxidative coupling catalyst and oxygen at a temperature ranging from 30° to 150° C.

The alkylbenzene solvent may be selected from toluene, ethylbenzene and propylbenzene and others wherein said alkyl group has up to about 10 carbon atoms. The amount of solvent required is dependant upon the solubility of the diphenoquinone and the reaction rate desired. Usually a diphenoquinone concentration of 5–50% by weight is economical.

The hydrogenation is carried out in the presence of from 0.1–10% by weight of a heterogeneous catalyst selected from a nobel metal such as ruthenium, platinum and palladium and transition metals such a nickel and copper which may be deposited on an inert substrate such as carbon, silica, alumina, diatomaceous earth, clay etc. These catalyst are well known and may be purchased commercially.

The reaction is carried out at temperatures of 25° to 150° C. and preferably about 5°–10° C. below the boiling point of the solvent at hydrogen pressures ranging from atmospheric to 100 psi. Most favorable reaction rates are obtained at temperatures of 125° to 145° C. and preferably 130° C. The reaction is usually complete at these temperatures within about 2 hours.

In the general operation of the invention the heterogeneous hydrogenation catalyst was placed into a suitably designed reaction vessel fitted with a reactant inlet and product outlet along with heating means as well as an entrance and exit means for the hydrogen containing gas. The reactor was also equipped with an agitator.

The reactor vessel was next charged with a solution of the tetraalkyl diphenoquinone in the alkylbenzene solvent, sealed and heated to the desired reaction temperature and thereafter controlled at that temperature and pressure with hydrogen gas under agitation for a period of about 2 hours. Complete reduction is indicated by the decoloration of the solvent. The heterogeneous catalyst may be removed from the hot solvent by filtration after which the solution containing the tetraalkyl biphenol is cooled to ambient temperature at which point the product precipitates from solution and is easily removed by further filtration. The solvent may be recycled for reuse or retained with the biphenol for the purposes of performing a transalkylation reaction. If preferred the solvent can be removed by distillation at a temperature below the thermal decomposition point of the tetraalkylbiphenol derivative after the catalyst is removed.

A better understanding of the invention may be had by reference to the following examples which are intended to illustrate but not limit the invention. All proportions are expressed in parts by weight unless otherwise specified.

EXAMPLE 1

3,3',5,5'-tetra-tert.-butyldiphenoquinone 20 grams (0.049 mol) and 200 milliliters (175 grams) 1.65 mols of ethylbenzene were placed in a 1 liter thick walled glass pressure vessel along with 1 gram of catalyst (5% ruthenium on carbon substrate). The vessel was sealed and degassed after which hydrogen gas was introduced through an inlet port at 20 psi. The reaction mixture was then heated to 130° C. for 2 hours under vigorous stirring. The completion of the reduction is indicated by the decoloration of the solvent from dark red to colorless. The reaction mixture was then cooled to room temperature, the catalyst separated by filtration under nitrogen blanket to avoid reoxidation and washed with 10 mls hydrogen saturated ethylbenezene solvent. The yield was estimated to be above 95% conversion to 3,3',5,5'-tetra-tert.-butyl-biphenol.

EXAMPLE 2

The procedure of Example 1 was repeated using 1 gram of catalyst (5% platinum on carbon substrate) at a reaction temperature of 135° C. for 1.5 hours under 20-30 psi hydrogen pressure.

EXAMPLE 3

Example 1 was repeated in the presence of 1.5 grams of catalyst (1% platinum on carbon substrate) at 130° C. under hydrogen pressure of 20-30 psi and completed within 1.5 hours.

EXAMPLE 4

The procedure of Example 1 was repeated using 200 ml of toluene solvent and was hydrogenated in the presence of 0.4 grams of catalyst (5% platinum on carbon) at 110° for 1 hour under hydrogen pressure of 30 psi. The yield was estimated to be greater than 90% of the tetra-tertiary-butyl-biphenol.

The biphenol solvent solutions remaining after the separation of the heterogeneous catalyst may be further subjected to a dealkylation/transalkylation reaction for the purpose of preparing pure biphenol and an alkylbenzene derivative substituted in the para position with a tertiary or secondary alkyl group in high yields.

The dealkylation/transalkylation reaction is carried out in an alkylbenzene solvent solution of a tetraalkyl substituted biphenol having the general formula:

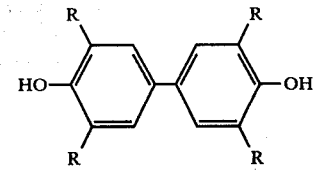

wherein R is a tertiary alkyl group having 4-8 carbon atoms such as tert-butyl, tert-pentyl and tert-octyl. The alkylbenzene solvent may be selected from toluene, ethylbenzene and propylbenzene and alkyl benzenes having up to about 10 carbon atoms in the alkyl group. The amount of solvent required is dependent on the solubility of the biphenol derivative and the reaction rate desired. Normally a biphenol concentration ranging from 5 to 50% by weight is economical.

The dealkylation/transalkylation reaction is carried out in the presence of a strong acid catalyst in concentrations such that the rate of reaction and yield at 100°-200° C. is economic. When strong acids are present such as fluorosulfonic acids the mol ratio of acid/tetraalkylbiphenol starting material may be less than one. However, when weaker acids such as alkyl or aryl sulfonic acids are used at least equimolar amounts are preferred. The catalyst material may be a liquid, a solvent soluble liquid, a solvent soluble solid or an acid distributed on or part of an insoluble substrate. Such catalysts are usually referred to as Friedel-Crafts type catalysts (Lewis acids) and may be selected from alkyl or aryl sulfonic acids such as methane sulfonic acid or para toluene sulfonic acid, or an acid type ion exchange resin such as Amberlyst ®-15 and a sulfonated fluorocarbon vinyletherpolymer such as Nafion ® 117 (Du Pont) having as the catalytic active sight —CF$_2$C-F$_2$—SO$_3$H groups.

The dealkylation reaction should be carried out in an inert atmosphere for a time sufficient to convert substantially all the substituted biphenol starting material to 4,4'-biphenol and the R-substituted alkylbenzene derivative. The amount of alkyl benzene solvent present in the reaction mixture should be at least 4 mols per mol of tetraalkyl substituted biphenol starting material and preferably 4-8 mols/mol. The length of time required to achieve substantially complete alkylation and transalkylation will depend primarily upon the operating temperature, concentration of the tetra substituted biphenol, catalyst concentration and agitation. For example, when using 2,2',6,6'-tetra-tert-butyl-4,4'-biphenol as a starting material a temperature of 100°-200° C. and preferably 120°-150° C. is preferred at pressures ranging from atmospheric to 100 psi.

The solid material separated from the liquid by decantation or filtration contains 4,4'-biphenol and the acid catalyst, for example methane sulfonic acid, which is a liquid, can be mostly separated from the 4,4'-biphenol by filtration under reduced pressure. Precipitation with water from an acetone solution removes the remaining acid yielding the 4'4'-biphenol at a purity of 99+%. No sublimation is necessary. The liquid phase consists of the alkyl benzene and the alkylated alkyl benzene as the co-product. In case where 2,2',6,6'-tetratert-butyl-4,4'-biphenol is the starting material and ethylbenzene is the solvent the ratio of the para to meta isomer of tert-butyl ethylbenzene is 90:10. Tert-butyl ethylbenzene and ethylbenzene can be easily separated by fractionate distillation. Solid acid catalysts offer the advantage of avoiding water for the precipitation of the biphenol and can be reused without further treatment.

While procedures described in the above examples for the manufacture of the tetra substituted biphenol starting material are preferred any well known technique for obtaining the tetra substituted diphenoquinone starting material may be employed.

The dealkylation/transalkylation process may be understood by reference to the following but not limiting examples:

EXAMPLE 5

The filtrate resulting from Example 1 was placed into another 1 liter heavy walled glass vessel along with 9 grams (0.053 mole) of methane sulfonic acid, sealed and degassed and pressurized with hydrogen to 5 psi. The glass reactor was placed into an oil bath heated to a temperature of 130° C. and stirred vigorously for about 2 hours. As the reaction proceeded 4,4' biphenol precipitated out. After cooling to room temperature the excess ethylbenzene and newly formed tert-butylethylbenzene was poured off from the wax-like precipitate consisting of 4,4' biphenol and methane sulfonic acid. When subjected to gas liquid chromatography the ethylbenzene solution of tert-butylethyl benzene was found to have a para/meta isomer ratio of 9:1. The wax-like precipitate was then removed from the reactor, placed on a filter and a dark red liquid mostly methane sulfonic acid was recovered. The residual material was dissolved in about 80 milliliters acetone at 50° C., diluted with 3–4 volumes of water at which point a white precipitate of 4,4' biphenol was collected and dried to yield 8.3 grams of 4,4'-biphenol equivalent to 91.5% yield. Upon recrystallization the crystalline product was subjected to IR and HPLC analysis and was found to be 99.4% pure. Tert-butyl-ethylbenezene was separated in a yield of 75% from ethylbenzene by distillation at 124° C. at 23 millimeters Hg over a 1 foot Vigreux column.

EXAMPLE 6

The catalyst free solution remaining from Example 2 was combined in a 1 liter thick walled glass reactor with 20.6 grams (0.108 mol) of para-toluene sulfonic acid hydrate, sealed under hydrogen and stirred for 2 hours at 150° C. After cooling to room temperature the precipitate and supernatent solvent solution was analysed as described in Example 5 after which a yield of 8.9 grams (88%) of 4,4' biphenol was obtained.

EXAMPLE 7

The ethylbenzene solution of Example 3 was placed into the previously described reactor with 9 grams of technical grade methane sulfonic acid (containing 30% water). The water was removed by azeotropic distillation with toluene, since the presence of water inhibits the transalkylation. After 90 minutes at 130° C. the reaction mixture was cooled to room temperature and worked up as described in Example 5 for a yield of 8.2 grams (90%) 4,4'-biphenol.

EXAMPLE 8

The toluene solvent solution collected from Example 4 was placed in a 1 liter heavy walled reactor along with 8 grams of methane sulfonic acid and heated under agitation for 2 hours at 120°–130° C. The products were separated according to the procedure of Example 5. 8.1 grams of 4,4'-biphenol (98% yield) was collected.

EXAMPLE 9

10 g (24.5 mmole) 3,3',5,5'-tetra-tert-butyl-diphenoquinone, 0.1 g 5% Pd/C, and 50 g ethylbenzene were placed in a heavy walled bottle, sealed with a rubber liner and metal cap, and 15 psi $H_2$ pressure were introduced. The reactor equipped with a magnetic stirring bar was placed in an oil bath at 125° C. The pressure rose to 25 psi $H_2$, which was maintained. After 2 hours the dark red color of diphenoquinone had disappeared indicating the complete hydrogenation to 4,4'-bis(2,6-di-tert-butyl-phenol). The reaction mixture was cooled to about 80° C. and the catalyst removed by anaerobic filtration and washing with ethylbenzene. The filtrate was transferred to another heavy walled bottle containing a magnetic stirring bar and 10 g of the strong acid resin Amberlyst ® 15, a sulfonated, macroporous copolymer of styrene and divinylbenzene obtained from Rohm and Haas in an air dried state. The reactor was kept in an oil bath at 150° C. for 3 hours while the magnetic stirrer agitated the reaction mixture. During this time a solid white material appeared. After cooling down to room temperature the acid catalyst and the precipitated 4,4'-biphenol were removed from the reaction mixture by filtration and washed with ethylbenzene. The filtrate contained 13.6 g (84.0 mmole) p- and m-tert-butyl-benzene (85.7% yield). The ratio of the para to meta isomer is again 9:1. The product 4,4'-biphenol was separated from the catalyst with acetone, from which 3.9 g (20.9 mmole) 4,4'-biphenol were obtained in 85.5% yield as white crystals.

EXAMPLE 10

10 g (24.5 mmol) of 3,3',5,5',-tetra-tert-butyl-diphenoquinone in 40 ml of ethylbenzene was hydrogenated as in Example 9. The filtered reaction mixture containing 4,4'-bis(2,6-di-tert-butylphenol) was transferred to a heavy walled bottle containing a magnetic stirring bar and as strong solid acid 9 g of Nafion ® 117, which was obtained from the Du Pont Company as a film, which was cut into small pieces, treated with conc. HCl at 70° C. for one hour, washed with water and acetone and dried in an oven at 70° C. over night. The reactor was placed in an oil bath at 170° C. with stirring. The dealkylation was completed within 30 minutes. 3.8 g (20.4 mmol) of 4,4'-biphenol was obtained in the same way as described in Example 9 (83.3% yield). The filtrate containing 14.3 g p- and m-tert-butyl-ethylbenzene was placed in a popbottle containing 0.2 g 5% Pd/C, 10 g 3,3',5,5',-tetra-tert-butyl-diphenoquinone, and magnetic stirring bar. The hydrogenation was completed after 3 hours at 130° C. under 25 psi $H_2$ pressure. The removal and washing of the catalyst was done as described above. The filtrate was transferred to a popbottle containing a magnetic stirring bar and the catalyst from the previous dealkylation, which had been treated with conc. $HNO_3$, washed with acetone and water and dried at 70° C. overnight. The reaction mixture was kept at 170° C. for 45 minutes, cooled and worked up in the same way as above. 3.9 g (20.9 mmole) of 4,4'-biphenol was obtained (85.5% yield). The filtrate contained 22.2 g of p- and m-tert-butyl-ethylbenzene (69.9% yield).

EXAMPLE 11

10 g (24.5 mmole) of 3,3',5,5',-tetra-tert-butyldiphenoquinone in 40 ml ethylbenzene was hydrogenated as in Example 9. The filtrate was transferred to a popbottle containing 1.5 g (10 mmol) trifluoromethane sulfonic acid and a magnetic stirring bar. The reaction mixture was kept at 120° C. for 45 minutes. 4 g of 4,4'-biphenol was obtained as white material after recrystallization from acetone (88% yield). The filtrate contained 13.8 g (85.2 mmol) of p- and m-tert-butyl-ethylbenzene (86.9% yield).

What is claimed is:

1. An improved process for making 4,4'-biphenol and an R-substituted alkylbenzene which comprises the steps of:

(a) forming a tetralkyl 4,4'-biphenol by the hydrogenation of a diphenoquinone having the general formula:

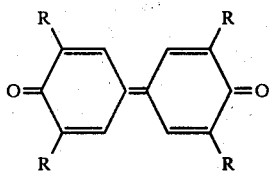

wherein R is a tertiary alkyl group having 4-8 carbon atoms employing hydrogen gas at pressures ranging from atmospheric to 100 psi and 0.1-10% by weight of a heterogeneous catalyst selected from noble and transition metals in a solvent solution of an alkyl benzene at temperatures ranging from 5°-10° C. below the boiling point of said solvent, (b) removing said catalyst from the tetraalkyl biphenol containing solution, (c) heating said solution at temperatures ranging from 100°-200° C. at pressures ranging from atmospheric to 100 psi in the presence of a strong Lewis acid catalyst in an inert atmosphere to form 4,4'-biphenol and an R-substituted alkylbenzene derivative, and (d) recovering 4,4'-biphenol and said R-substituted alkylbenzene from said solution.

2. A process of claim 1 wherein said R-groups are selected from tert-butyl, tert-pentyl and tert-octyl.

3. A process of claim 1 wherein the concentration of diphenoquinone in said solution is such that the mol ratio of alkylbenzene solvent to said diphenoquinone is at least 4/1.

4. The process of claim 1 wherein said reaction in step (a) is carried out in the presence of from 0.1-10% by weight of heterogeneous catalyst selected from the group consisting of platinum, ruthenium, palladium, nickel and copper.

5. The process of claim 4 wherein said catalyst is deposited on an inert substrate.

6. A process of claim 1 wherein step (a) is carried out at a temperature of 25°-150° C.

7. A process of claim 1 wherein said alkyl benzene solvent has an alkyl group having up to 10 carbon atoms.

8. A process of claim 7 wherein said solvent is selected from toluene, ethylbenzene and propylbenzene.

9. A process of claim 6 wherein said temperature ranges from 125°-145° C.

10. A process of claim 1 wherein step (c) is carried out at 120°-150° C.

11. A process of claim 1 wherein step (c) is carried out in the presence of a strong acid catalyst selected from alkyl, aryl sulfonic acids and polymers containing sulfonic acid groups.

* * * * *